(12) United States Patent
Crow et al.

(10) Patent No.: US 7,313,483 B2
(45) Date of Patent: Dec. 25, 2007

(54) DIVE COMPUTER AND METHOD FOR DETERMINING GAS FORMATION

(76) Inventors: Steven Crow, 2418 S. Milwaukee St., Denver, CO (US) 80210; John Lewis, 4524 Palos Verdes Dr. East, Rancho Palos Verdes, CA (US) 90275

( * ) Notice: Subject to any disclaimer, the term of this patent is extended or adjusted under 35 U.S.C. 154(b) by 0 days.

(21) Appl. No.: 11/256,304

(22) Filed: Oct. 21, 2005

(65) Prior Publication Data

US 2006/0253265 A1 Nov. 9, 2006

Related U.S. Application Data

(60) Provisional application No. 60/678,894, filed on May 5, 2005.

(51) Int. Cl.
*G06F 19/00* (2006.01)
(52) U.S. Cl. ............... 702/23; 702/138; 73/865.1
(58) Field of Classification Search ............. 702/23; 73/865.1
See application file for complete search history.

(56) References Cited

U.S. PATENT DOCUMENTS

| | | | | |
|---|---|---|---|---|
| 4,753,117 | A | * | 6/1988 | Osterhout et al. ......... 73/865.1 |
| 5,363,298 | A | * | 11/1994 | Survanshi et al. ........ 73/865.1 |
| 5,457,284 | A | * | 10/1995 | Ferguson ............... 128/201.27 |
| 6,931,348 | B2 | * | 8/2005 | Furuta et al. ............... 702/138 |

OTHER PUBLICATIONS

Crow, S. C. 2004 "Mathematical Formulation", Decompression Memo.
Crow, S. C. 2004 "First Order Solution", Decompression Memo.
Crow, S. C. 2004 "First Order Theory with Gas Formation and Transport", Decompression Memo.
Dick, A. P. K., Vann, R. D., Mebane, G. Y., and Feezor, M. D. 1984 "Decompression induced nitrogen elimination", Undersea Biomedical Research 11, No. 4, 369-380.
Hamilton, R. W., Rogers, et al., 1994 The DSAT Recreational Dive Planner: Development and validation of no-stop decompression procedures . . . , Diving Science and Tech Com and Hamilton Research Ltd. Tarrytown, New York.
Gernhardt M. L. 1991 "Development and Evaluation of a Decompression Stress Index Based on Tissue Bubble Dynamics", Thesis, University of Pennsylvania, pp. 33-37.

(Continued)

*Primary Examiner*—John Barlow
*Assistant Examiner*—Jonathan Moffat
(74) *Attorney, Agent, or Firm*—Kauth, Pomeroy, Peck & Bailey LLP

(57) ABSTRACT

The invention disclosed herein employs an algorithm, the Gas Formation Model ("GFM"), to calculate the formation of free gas in a human body. The GFM is based on a novel theory of the formation of free gas relative to the physiology of the human cardiovascular system. Additionally, the GFM utilizes a novel means for the solution of integro-differential equations, the type of equations that derive from the introduction of physiological parameters. GFM-based dive computers utilize novel inputs, including a measure of exercise at depth to reflect the state of an individual's cardiovascular system. GFM-based dive computers also produce novel outputs, including the actual volume of free gas present in a diver's cardiovascular system. The GFM is implemented as a practical computational tool by means of a incorporating the algorithm into a dive computer.

33 Claims, 10 Drawing Sheets

OTHER PUBLICATIONS

Hempleman, H. V. 1952 "A New Theoretical Basis for the Calculation of Decompression Tables", Medical Research Council Report UPS 131, London.

Hills B. A. 1966 "A Thermodynamic and Kinetic Approach to Decompression Sickness", Thesis, Libraries Board of South Australia, University of Adelaide, 165-167.

Hills, B. A. 1977 Decompression Sickness. vol. 1. The Biophysical Basis of Prevention and Treatment. John Wiley and Sons, Ltd. New York, pp. 115-116, 244-247.

Knapp, R. T., Daily, J. W., and Hammitt, F. G. 1970 Cavitation, McGraw-Hill, New York, pp. 58-67.

Lewis, J. E. and Shreeves, K. W. 1993 Decompression Theory, Dive Tables, and Dive Computers, Second Edition, International PADI Inc., Santa Ana, California.

Lewis, J. E. 2004 "A New Approach to Decompression Theory", Proposal to the US Navy Deep Submergence Biomedical Development, Oceanic USA.

Lewis, J.E., 2005 Private communication.

Pilmanis, A. A. 1976 "Intravenous Gas Emboli in Man after Compressed Air Ocean Diving", Office of Naval Research Report N00014-67-A-0269-0026, Washington D.C.

Scanlon, V. C., and Sanders, T. 1999 Essentials of Anatomy and Physiology, 4th Edition, F. A. Davis and Co., Philadelphia, p. 292.

Spencer, M. P. 1976 "Decompression Limits for Compressed Air Determined by Ultrasonically Detected Bubbles", J. Appl. Physiology 40, 229-235.

Thibodeau, G. A. and Patton, K. T. 2000 Structure and Function of the Body, 12th Edition, Mosby, St. Louis, Missouri, pp. 300-326.

Vann, R. D. and Thalmann, E. D. 1993 The Physiology and Medicine of Diving, 4th Edition, Chapter 14, W. B. Saunders and Company, Philadelphia, p. 392.

Weathersby, P.K. and Homer, L. D. 1980 "Solubility of inert gases in biological fluids and tissues: a review", Undersea Bio. Res., 7, 277-296.

Wienke, B. R. Basic Decompression Theory and Application, Second Edition, Best Publishing Company, Flagstaff, Arizona, pp. 130-131.

Behnke, A. R. and Willmon, T. L. 1941 "Gaseous nitrogen and helium elimination from the body during rest and exercise", Am. J. Physiol., 131, 619-626.

Boycott, A. E., Damant, G. C. C., and Haldane, J. S. 1908 "The Prevention of Compressed Air Illness", J. Hyg. Cambridge 8, 342-443.

Burton, A. C. 1968 "Physiology and biophysics of the circulation", Year Book Medical Publishers Inc., Chicago, pp. 62-64.

Caro, C. G., Pedley, T. J., Schroter, R. C., and Seed, W. A. 1978 The Mechanics of the Circulation, Oxford University Press, New York, pp. 352-357.

Carslaw, H. S. and Jaeger, J. C. 1976 Conduction of Heat in Solids, Clarendon Press, Oxford, England, pp. 278-280.

Crow, S. C. 2004 "Gas Sheets to Bubbles", Decompression Memo.

Crow, S. C. 2004 "Surface Energetics", Decompression Memo.

Crow, S. C. 2004 "Tension and Solubility", Decompression Memo.

Crow, S. C. 2004 "Duhamel's Integral Solution of the Diffusion Equation", Decompression Memo.

Crow, S. C. 2004 "Toward a Criterion for Gas Layer Formation", Decompression Memo.

Wienke B. R. 1990 "Reduced Gradient Bubble Model", Int. J. Biomed. Comp. 26, 237-256.

Workman R. D. 1965 Calculation of Decompression Schedules for Nitrogen-Oxygen and Helium-Oxygen Dives. US Navy Experimental Diving Unit Report, NEDU 6-65, Washington D.C.

Xu, X. G., Chao, T. C., and Bozkurt, A. 2000 "VIP-Man: An image-based whole-body adult male model constructed from color photographs of the visible human project for multi-particle Monte Carlo calculations", *Health Phys.* 78. 476-486.

Yount et al., "On the Use of a Bubble Formation Model to Calculate Diving Tables", Aviation, Space and Environmental Medicine, Feb. 1986, pp. 149-156.

\* cited by examiner

| Depth | Powell | PADI | Pelagic | GFM |
|---|---|---|---|---|
| 40 |  | 140 | 138 | 121 |
| 45 | 100 |  | 102 | 92 |
| 50 |  | 80 | 79 | 74 |
| 55 | 65 |  | 65 | 61 |
| 60 |  | 55 | 56 | 52 |
| 65 | 45 |  | 48 | 45 |
| 70 |  | 40 | 40 | 39 |
| 75 | 35 |  | 35 | 34 |
| 80 |  | 30 | 31 | 31 |
| 85 | 27 |  | 28 | 27 |
| 90 |  | 25 | 25 | 25 |
| 95 | 22 |  | 22 | 22 |
| 100 | 20 | 20 | 20 | 20 |
| 110 | 17 | 16 | 17 | 16 |
| 120 | 14 | 13 | 14 | 14 |
| 130 | 12 | 10 | 12 | 12 |

FIG. 8

DIVE COMPUTER AND METHOD FOR DETERMINING GAS FORMATION

This application claims the benefit of U.S. Provisional Application No. 60/678,894, filed May 5, 2005.

BACKGROUND OF THE INVENTION

1. Field of the Invention

This invention is related in general to the field of dive computers. In particular, the invention consists of a method for calculating the formation of free gas in a human body due to a change in altitude, depth, or pressure.

2. Description of the Prior Art

An undersea diver needs to breathe air or some other gas mixture at a pressure that closely matches the pressure of the surrounding water. The pressure exerted on the diver increases dramatically as he increases his depth under the surface of the water. As a result, the concentrations or 'tensions' of dissolved inert gases in his body tissue can rise well beyond the levels than are common above the water surface.

Of special consequence is the inert gas nitrogen, which comprises 79% of the volume of air under normal atmospheric conditions. During a dive, excess nitrogen becomes dissolved in the body's tissues. The amount of nitrogen which is absorbed by the body's tissues is a function of the depth of the dive and the amount of time at this depth.

While dissolved, the nitrogen undergoes no reactions with the tissue. However, as the diver rises to the surface, the nitrogen leaves the body's tissues and travels through the diver's bloodstream, where it may be released as free gas. This released free gas may result in decompression sickness, which can result in pain, disability, or death of the diver. In order to reduce the likelihood of decompression sickness, a diver may need to slowly rise to the surface or stop at intervals along the way.

Decompression Sickness

Decompression sickness made its first appearance in the mid-nineteenth century among men who worked in submerged caissons to set the footings of bridges like the Brooklyn Bridge. At the time, the affliction was called caisson workers' disease. The symptoms were acute joint pain following emergence from the high pressure atmosphere in the caissons. Victims would often bend over in pain, so the affliction became commonly known as "the bends". The bends were clearly caused by the fall in air pressure or "decompression" as the victims passed from submerged caissons to the surface, but the physiology remained otherwise obscure, an obscurity that persists to some degree today.

Haldane Models

The first systematic studies of caisson disease or decompression sickness were conducted at the start of the last century, stimulated by the appearance of the same symptoms among deep sea divers, who were subject to the same type of decompression as caisson workers. That early research culminated in a brilliant paper by Haldane and co-workers, who argued that "compressed air sickness" is caused by absorption of nitrogen in tissue during the compressive phase of a dive, followed by its release in gaseous form during decompression (Boycott, Damant, and Haldane 1908). Haldane and his group conducted extensive pressure chamber tests on goats and compared the results with divers' experience.

The Haldane group also developed a mathematical model of decompression sickness based on the idea that tissue absorbs nitrogen at a rate proportional to the difference between the partial pressure of nitrogen in the lungs and the "tension" of nitrogen dissolved in tissue and blood. They discovered that absorption at a single rate would not explain their data, and they conceived the idea of multiple "tissue compartments" with different rates of nitrogen absorption. Multiple tissue compartments with different absorption rates have come to be known as the "Haldane model". Almost 100 years after its conception, the Haldane model remains the basis for today's dive computers.

The Haldane group posited five tissue compartments with absorption rates equivalent to half times of 5, 10, 20, 40, and 75 minutes. They assumed that a diver would suffer decompression sickness if the nitrogen tension in any one of the compartments reached a specific load common to all of the compartments. The nitrogen load was measured not in terms of concentration (ml/ml) or tension (mm Hg) but in terms of the depth where the nitrogen concentration would be in equilibrium with the air being breathed. Thus the critical nitrogen load was expressed in terms of feet of sea water (fsw).

Subsequent workers increased the number of hypothetical tissue compartments and assigned to them different critical nitrogen loads. Workman (1965) proposed six tissue compartments with half times of 5, 10, 20, 40, 80, and 120 min and assigned to them critical loads ranging from 100 down to 20 fsw. Workman's variant of the Haldane model became the basis for the US Navy dive tables and for the first generation of dive computers (Lewis and Shreeves 1993). More recent dive computers have increased the number of hypothetical compartments to twelve, and Lewis and Shreeves even invoke the ultimate dive computer HAL with 1530 tissue compartments and 3060 half times and loads! However, Hills (1977) has observed with amusement that the larger Haldane models have more parameters than data available to be fitted by them.

The largest relevant data set was published by Hamilton, Rogers, Powell, and Vann (1994) under the title "The DSAT Recreational Dive Planner". The data are the results of 2943 dives, some in water, and some simulated in a pressure chamber at the Institute of Applied Physiology and Medicine in Seattle. To determine dive profiles with low risks of decompression sickness, they fitted the parameters of a Haldane model to an earlier data set of Spencer (1976). Only 301 or 10% of those dives produced measurable bubbles, and only one caused decompression sickness, an incidence rate of 0.03%. The Haldane parameters established by Hamilton et al. are the basis for many of the dive computers in use today.

Other Models

Despite their widespread use, the Haldane models invite some reservations. One is the notion of "tissue compartments", which never have been correlated with physiological structures. Another is "perfusion", the means by which gas is supposed to travel from the lungs into tissue. Perfusion describes the Haldane models but not an actual gas transport mechanism.

Among the first to try to improve upon those concepts was Hempleman (1952), who suggested that gas absorption could be modeled as a process of diffusion from blood vessels into homogeneous tissue. He first modeled the tissue as a one-dimensional slab bounded on one side by blood and unbounded on the other. An immediate result of that very simple model is that the mass of nitrogen absorbed during a dive is proportional to the partial pressure P of nitrogen above its value at sea level times the square root of the duration T of the dive. Hempleman assumed that the product "P-root-T" must remain below some allowable value for safe return to the surface. He determined the allowable limit by comparison with Workman's data, with the result that P-root-T is around 500 fsw-$\sqrt{\min}$. In 1968, Hempleman's simple model became the basis for the Royal Navy Dive Tables.

However, one-dimensional diffusion into an infinite slab could not allow for saturation, since the slab would absorb nitrogen indefinitely. To allow for saturation, Hempleman analyzed diffusion into a finite slab and obtained an infinite series of terms bearing a resemblance to Haldane "tissue compartments". The finite slab model did not improve agreement with Workman's data and may never been used for dive computers.

The most obvious limitation of both the Haldane and Hempleman models is that they make no attempt to predict the formation of free nitrogen gas, the presumptive cause of decompression illness. The emphasis instead is on nitrogen storage in form of molecules dissolved in tissue. This lack to attention to a model for free gas formation is particularly odd for the Haldane group, who observed nitrogen gas bubbles in the eyes of severely afflicted goats.

Hills (1966, 1977) may have made the first serious effort to understand gas formation as a cause of decompression sickness. He proposed that gas volumes form in tissue wherever net gas tension exceeds the local ambient pressure, and he drew attention to the fact that any such gas cells would contain the so-called metabolic gases, oxygen, carbon dioxide, water vapor, and nitrogen. Many of Hills's physiological insights were brilliant, but they were not pulled together into a mathematical model of decompression sickness. Additionally, his qualitative proposal for gas formation would have resulted in calculations indicating far too much gas being formed in tissue, e.g., several liters for dives to 100 ft. Also, his proposed ascent strategies are clearly at odds with the experience of divers (Gernhardt 1991).

A nitrogen gas concept finally made its way into Haldane models as RGBM, the Reduced Gradient Bubble Model (Wienke 1990, 2003). The basic idea is that nitrogen filled microbubbles pervade body tissue at all times, even without dives and ascents. Without a special sustaining mechanism, gas in the hypothetical bubbles would diffuse into surrounding tissue in minutes, and the bubbles would close. Wienke assumes that "flexible seed skins" keep the bubbles open while a diver is on the surface or descending under water. During ascent, gas diffuses into the microbubbles, and they enlarge in accord with Boyle's law for expansion at constant temperature. The presumed presence of the bubbles reduces the allowable nitrogen loads of the Haldanian tissue compartments. The Gradient in the Reduced Gradient Bubble Model is proportional to the difference between the allowable Haldane tissue compartment loads and the partial pressure of nitrogen at sea level.

However, the Reduced Gradient Bubble Model has to assume the perpetual existence of gas bubbles held open by "flexible seed skins". The concept of perpetual gas bubbles, moreover, conflicts with the common observation that bubbles in supersaturated liquids form on boundaries, not in the interiors of liquids (Knapp, Daily, and Hammitt 1970). The Reduced Gradient Bubble Model does not supercede the Haldane models, but rather changes the allowable nitrogen loads in response to specific dive scenarios, e.g., reversed dive profiles. Finally, the Reduced Gradient Bubble Model is not a real-time algorithm. RGBM computations are traditionally performed on a mainframe computer and incorporated into dive computers as modified Haldane allowable nitrogen loads.

Based on these models, the sport diving industry has developed dive computers to guide divers with regard to allowable times at depth and ascent procedures to avoid decompression sickness. Traditional dive computers measure time and water pressure, and perform computations to indicate the time a diver may remain at a particular depth and the recommended ascent procedures to minimize the possibility of decompression sickness.

However, these algorithms are not based on physiology and make no prediction with regard to the formation of free nitrogen. As a consequence, the algorithms are of uncertain validity when used outside of the dive data upon which they are based. Accordingly, it is desirable to have a dive computer that utilizes an algorithm to calculate the potential formation of free nitrogen when utilized in conditions outside of those covered by existing dive tables.

Because these dive computers do not incorporate physiological parameters as inputs, the algorithms cannot be tuned with any certainty to the needs of individual divers. Also, because existing algorithms are not based on physiology, they cannot be upgraded with modern research in physiology. Accordingly, it is desirable to have a method of calculating the potential formation of free nitrogen in the human body that can take into account physiological parameters of the user.

SUMMARY OF THE INVENTION

The invention disclosed herein employs an algorithm, the Gas Formation Model ("GFM"), to calculate the formation of free nitrogen in a human body. The GFM is based on a novel theory of the formation of free nitrogen relative to the physiology of the human cardiovascular system. Additionally, the GFM utilizes novel means for the solution of integro-differential equations, the type of equations that derive from the introduction of physiological parameters. The GFM is implemented as a practical computational tool by means of a incorporating the algorithm into a dive computer, which may be about the size of a wrist watch.

GFM-based dive computers can utilize novel inputs, including a measure of exercise at depth to reflect the state of an individual's cardiovascular system. GFM-based dive computers also produce novel outputs, including the maximum volume of free nitrogen gas present in a diver's cardiovascular system following ascent. The evaluation, prediction, and display of free gas volume are important elements of this invention.

Various other purposes and advantages of the invention will become clear from its description in the specification that follows and from the novel features particularly pointed out in the appended claims. Therefore, to the accomplishment of the objectives described above, this invention comprises the features hereinafter illustrated in the drawings, fully described in the detailed description of the preferred embodiments and particularly pointed out in the claims. However, such drawings and description disclose just a few of the various ways in which the invention may be practiced.

BRIEF DESCRIPTION OF THE DRAWINGS

FIG. 8 is a table of gas formation model predictions of no-decompression limits, according to the invention.

DESCRIPTION OF THE PREFERRED EMBODIMENTS

Figure 1:
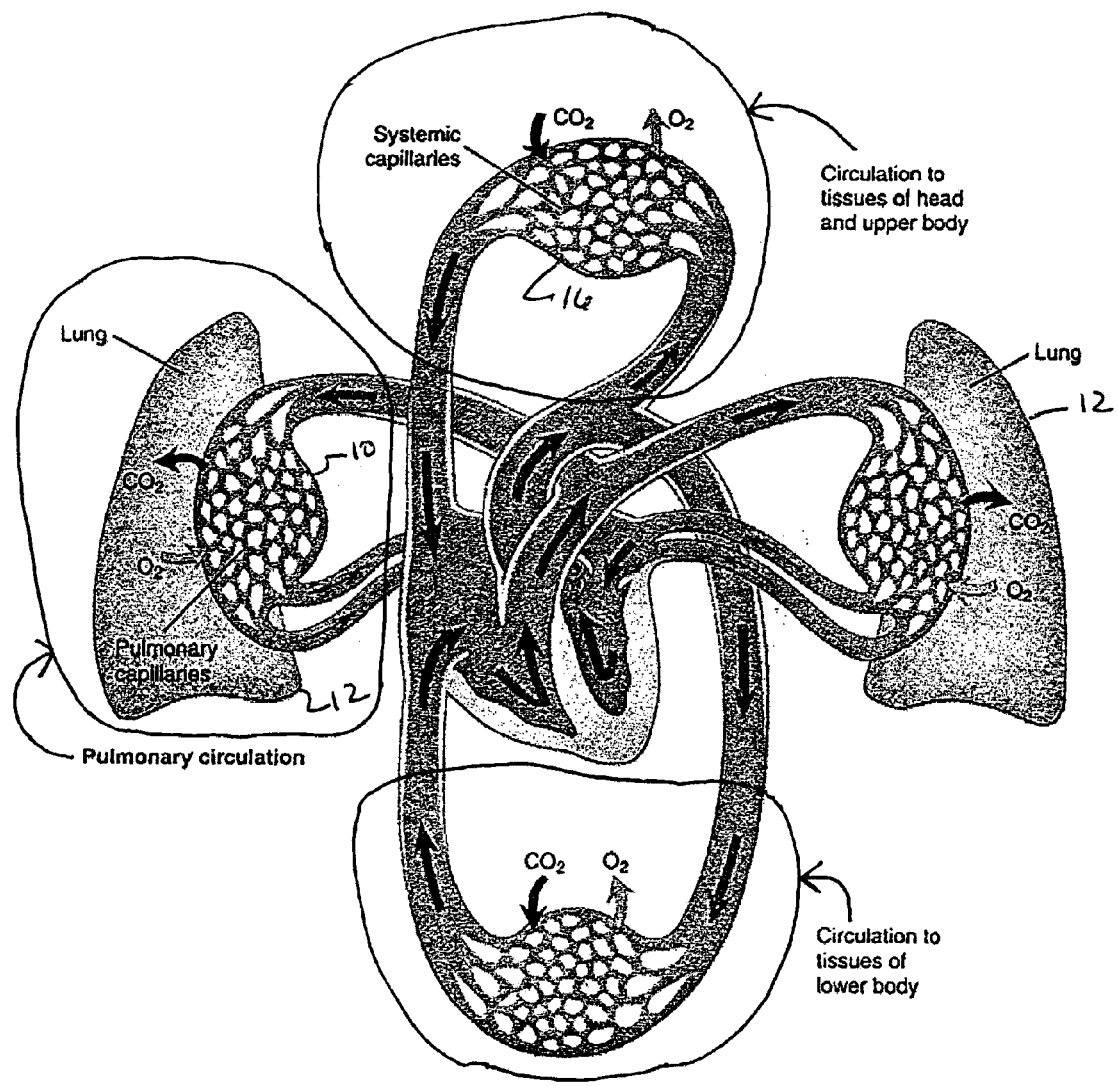
FIG. 1 is a diagram of a cardiovascular system.

This invention is based on the idea of using an algorithm to calculate the formation of free nitrogen in the human body. The invention disclosed herein may be implemented as a method, apparatus or article of manufacture using standard programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays ("FPGAs"), application-specific integrated circuits ("ASICs"), complex programmable logic devices ("CPLDs"), programmable logic arrays ("PLAs"), microprocessors, or other similar processing devices.

The gas formation model ("GFM") is based on the physics of gas formation in supersaturated substances and on the physiology of the human cardiovascular system. This requires an understanding of nitrogen gas formation during decompression, with nitrogen storage during compression as a mere precursor.

As with the Hempleman model, diffusion into tissue during compression must be accounted for. As with the Hills' model, a cylindrical diffusion geometry and metabolic gases must also be accounted for. However, a series of differential equations resembling Hempleman's finite slab model applied to Haldane's tissue compartments produces a novel means of solving a key integro-differential equation, i.e., the integral representing tissue "memory" of past nitrogen tension exposures.

Another element of the invention is the realization that a measurement of existing gas bubbles is not helpful in predicting subsequent formation of free nitrogen gas. Gas bubbles are certainly a signature of decompression sickness and are a useful diagnostic tool, but they are a consequence rather than a cause of gas formation. It is helpful to realize that the first manifestation of free gas is the production of gas layers, not gas bubbles.

Physics of Gas Formation:

Analyses and observations confirm a fact known from past literature (e.g. Knapp et al. 1970) that bubbles always form on surfaces rather than in the interiors of supersaturated liquids.

Gas bubbles associated with decompression illness start as gas sheets between blood and surrounding tissues. Because the gas sheets are too thin to see in casual tests like sudden decompression of carbonated water bottles, what an observer may see is bubbles that seem to grow from the walls. However, it has been determined that the bubbles result from instabilities in underlying sheets of gas.

This leads to the formation of a fundamental concept that gas sheets or layers are the original locales of free gas emerging from a solution. A surface between a liquid (blood) and solid (tissue) has a specific energy per unit area requirement for the passing of gas through the membrane of the tissue. However, more energy per unit area is required to bound a gas between the solid and the liquid. This is because the gas molecules dissolved in solids or liquids have both kinetic energy (due to vibration) and potential energy (also due to vibration), in equal amounts. When a gas layer forms, the vibrational potential energy of the gas molecules transforms into the required surface energy corresponds to the necessary surface tension.

Physiology

Boundaries within the body are the places where free nitrogen gas is likely to form during decompression. Conceivably such boundaries could be found in the interior of tissue, but gas pockets so formed would be constrained by the elasticity of the surrounding tissue and would likely diffuse back into the tissue.

Much more likely sites for the formation of gas layers are the boundaries between tissue and blood which are continuously swept away by the blood stream. Such gas layers are relatively flat and not subject to the strong compressive effects of surface tension which acts to force gas out of microbubbles. This formation of gas on the boundaries between tissue and blood accounts for the appearance of bubbles in the blood stream during decompression. These bubbles moving in the blood stream can be detected by Doppler velocimetry, a method often used as a measure of decompression stress (Pilmanis 1976).

By far the largest area of contact between tissue and blood resides in capillaries, the fine scale blood vessels responsible for most of the transfer of metabolic gases from blood to tissue and back. The diagram of FIG. 1 shows how capillaries are arranged in the cardiovascular system (Thibodeau and Patton 2000). The pulmonary capillaries 10 transfer dissolved gas between the lungs 12 and circulatory system, while the systemic capillaries 16 interface between blood and tissue. Probable sites for the formation of gas layers are the interior surfaces of the systemic capillaries 16.

The total surface area of the capillaries of an average person is about 600 square meters, or 6500 square feet. The formation of gas in systemic capillaries 16 accounts for the fact that gas emboli induced by decompression are almost always found in the veins downstream of those capillaries, and rarely in the upstream arteries. This also accounts for the profound effect of exercise on decompression phenomena (Dick, Vann, Mebane, and Feezor 1984). Many of the systemic capillaries 16 have precapillary sphincter muscle cells, which act as valves to close off the capillaries during periods of rest (Caro, Pedley, Schrotter, and Seed 1978). The sphincter valves open during periods of exercise, thereby greatly enlarging the capillary surface area exposed to blood flow and increasing the rate of gas transfer between blood and tissue. The experiments of Dick et al. show that exercise can increase the amount of nitrogen dissolved in tissue by a factor better than two.

GFM Input Parameters

The input parameters for a Haldane model are mostly half times and gradients selected to fit dive data. In contrast, most input parameters for the GFM pertain to human physiology, and many of these parameters are measures of the cardiovascular system, in particular the systemic capillaries 16, as follows:

| | |
|---|---|
| a | capillary radius (microns); |
| b | radius of surrounding tissue (microns); |
| L | capillary length (microns); |
| $S_b$ | solubility of nitrogen in blood (ml/ml); |
| $S_t$ | solubility of nitrogen in tissue (ml/ml); |
| $D_t$ | diffusivity of nitrogen in tissue (microns$^2$/min); |
| $v_b$ | average velocity of blood in capillary (microns/min); |
| $N_c$ | number of systemic capillaries; |
| θ | transpiration time for nitrogen gas from lungs (min). |

Values of these parameters are presented in Appendix A, which includes a listing of a current implementation of the GFM in Visual Basic code. Natural units are microns for length (one-millionth of a meter), mm Hg for pressure (millimeters of mercury), ml for gas volume (milliliters), and min for time (minutes). Microns are used for length because of the small size of capillaries, typically having radii of around 4 microns and lengths of approximately 1000 microns.

Other input parameters relate to the diver's blood pressure and tension of metabolic gases: oxygen, carbon dioxide, and water vapor. The general formula for metabolic ("other") gas pressure is:

$$p_o = p_{O2} + p_{CO2} + p_{H2O}. \quad (1)$$

using the following input parameters:

| | |
|---|---|
| $P_{oa}$ | metabolic pressure at arterial end of capillary (mm Hg); |
| $P_{ov}$ | metabolic pressure venous end of capillary (mm Hg); |
| $P_{ba}$ | blood pressure arterial end of capillary (mm Hg); |
| $P_{bv}$ | blood pressure venous end of capillary (mm Hg). |
| $P_{amb}$ | ambient pressure (mm Hg). It should be noted that the ambient pressure of the dive computer is a critical variable and is, therefore, continuously measured. |

Additional input parameters relate to gas mixtures, in particular the fraction of nitrogen when the diver breaths "nitrox" and the fraction of helium when the diver breathes "heliox" or "Trimix":

| | |
|---|---|
| $R_{N2}$ | fractional partial pressure of nitrogen. |
| $R_{He}$ | fractional partial pressure of helium. |

When a diver breaths air, the parameter $R_{N2}$ is 0.79, the fractional partial pressure of nitrogen in the atmosphere.

Two additional input parameters define computational resolution in time and space:

| | |
|---|---|
| delt | time step (min); |
| delx | spatial step along capillary (microns). |

Finally and importantly is time itself:
t time (min).

Many of these parameters, such as capillary radius a, length L, solubility $S_t$ of nitrogen in tissue, are fixed in the firmware of a GFM dive computer. Others are measured in real time or inferred from measurements of physiological variables. The time dependent parameters include time t itself, ambient pressure $p_{amb}$, the gas mixture fractions $R_{N2}$ and $R_{He}$, and the number $N_c$ of active systemic capillaries.

Exercise

As previously explained, exercise causes systemic capillaries to open up, increasing the capillary surface area available for the transfer of nitrogen from blood to tissue. This allows the tissue to store more nitrogen, resulting in a corresponding increase in the likelihood that gas may form during decompression as the nitrogen transfers from tissue to blood.

Exercise changes two of the GFM parameters, b and $N_c$, and, possibly the parameter $v_b$. As capillaries open up, the radius b characterizing the tissue attributable to each capillary decreases in such a way that the product $$V_t = N_c(t)\pi b^2(t)L \quad (2)$$

is preserved.

$V_t$ is the total volume of tissue surrounding all the capillaries. The capillary walls are inextensible, so their radius a changes little if at all. As a result, the ratio b/a decreases as the number of active capillaries increases. The ratio b/a has an important bearing on the memory integral described in the section on the GFM mathematical model and ultimately an important bearing on gas formation. $N_c$ and b/a, in turn, are related to the divers' level of exercise.

GFM dive computers can determine the diver's level of exercise in one or more of three ways:
1. by input from the diver as to his perceived level of exercise, e.g. rest, moderate (assumed default), or strenuous;
2. by continuous measurement of pulse rate; or
3. by continuous measurement of oxygen consumption, a direct measure of metabolic rate.

Mathematical Model

The mathematical model of gas formation starts with a set of first principles: convection and diffusion of nitrogen in blood; diffusion of nitrogen into tissue; diffusion of nitrogen from tissue during decompression; gas formation on the inside surfaces of capillaries; free gas transport in gas layers around blood streams; and gas transpiration out from the lungs. The GFM also involves a sequence of rational approximations, meaning approximations based on certain dimensionless groups.

The primary dependent variable of the mathematical model is the tension p(x,t) of nitrogen in the capillary blood stream. The word "tension" conveys a sense of mechanical stress, but it really is just a measure of concentration. A tension p means that the nitrogen concentration would be in equilibrium with free nitrogen gas at a partial pressure p.

The tension is a function of distance x along the capillary as well as of time t. The nitrogen tension p(0,t) at the entry of the capillary is the same as the tension of arterial blood and by assumption the same as the partial pressure of nitrogen in the alveoli of the lungs. Thus $$p(0,t) = R_{N2}[p_{amb}(t) - 47 \text{ mm Hg}], \tag{3}$$

where the correction within the square brackets takes into account the partial pressure of water vapor in alveoli. Since arterial tension is the same as alveolar partial pressure, equation (3) serves as a boundary condition at the upstream end of the capillary.

Two initial conditions are needed at all locations x along the capillary:

$$p(x,0) = p(0,0) \text{ and } \partial p(x,0)/\partial t = 0. \tag{4}$$

Both conditions are applied when the dive computer is turned on, but their effects disappear as a pressure history evolves. Nitrogen tension changes along the capillary in accord with an integro-differential equation:

$$S_b \pi a^2 v_b \frac{\partial p(x,t)}{\partial x} = -2\pi S_t D_t \int_{-\infty}^{t} \frac{\partial p(x,t')}{\partial t'} F\left[\frac{D_t(t-t')}{a^2}\right] dt'. \tag{5}$$

The left side of this equation represents the flow of nitrogen dissolved in the blood stream, and the right represents nitrogen diffusion into or from the surrounding tissue. F is a "memory function" that relates tension changes at past times t' to the current flux of nitrogen through the capillary surface. The memory function can be expressed as an infinite series, $$F\left[\frac{D_t(t-t')}{a^2}\right] = \pi \sum_{n=1}^{\infty} c_n \exp\left[-b_n^2 \frac{D_t(t-t')}{a^2}\right], \tag{6}$$

in which the $b_n$'s and $c_n$'s depend only on the ratio b/a. The constants $b_n$ are the eigenvalues of the cylindrical diffusion problem, and the terms in the series (6) are called eigenmodes. The eigenvalues are the roots of a rather complicated equation involving Bessel functions, $$J_0(b_n)Y_1(b_n b/a) - Y_0(b_n)J_1(b_n b/a) = 0, \tag{7}$$

and the equation for the $c_n$'s is even more complicated. Both can be found in standard texts on diffusion theory, for example Carslaw and Jaeger (1976).

Equation (5) prevails wherever the sum of p plus the metabolic pressures $p_o$ is less than the confining pressure, which in turn is the sum of ambient pressure $p_{amb}$ plus blood pressure $p_b$:

$$p(x,t) \leq p_{N2}(x,t) \equiv p_{amb}(t) + p_b(x,t) - p_o(x). \tag{8}$$

Figure 2:
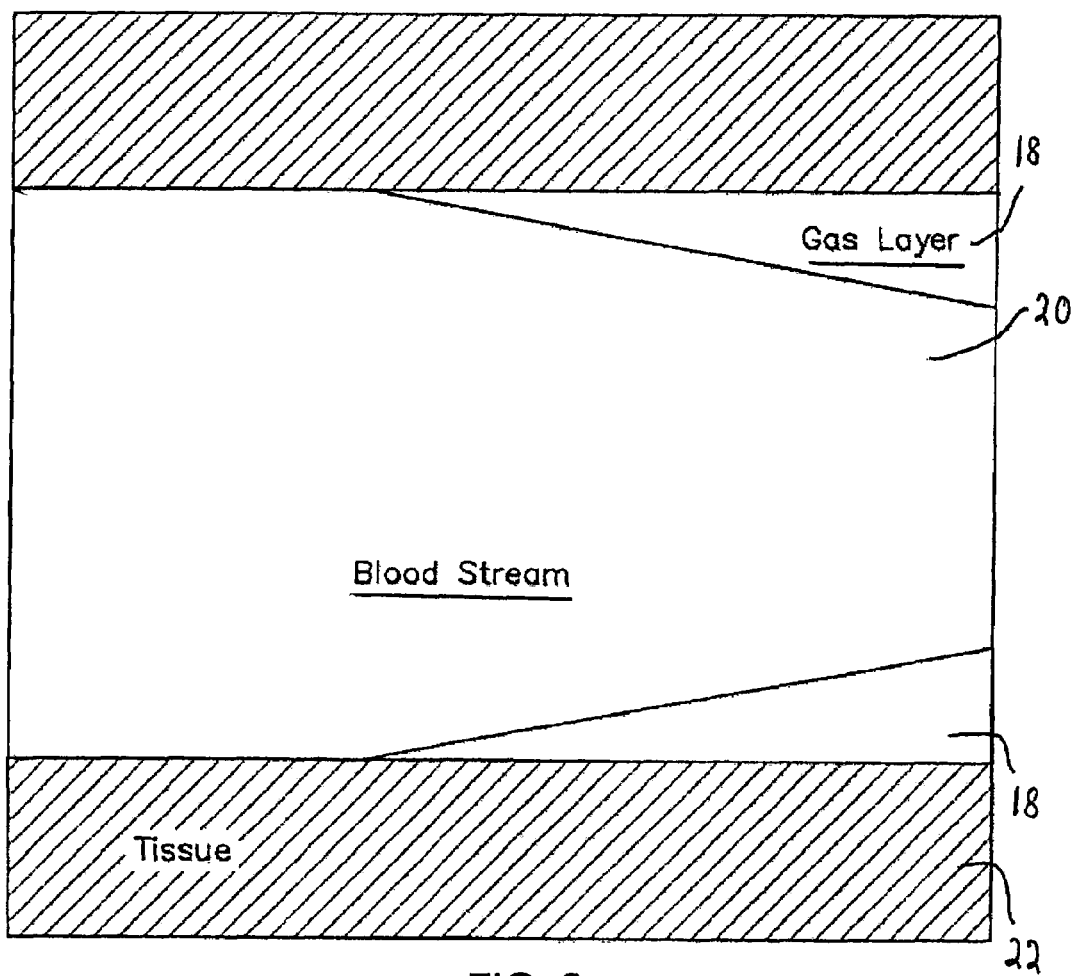
FIG. 2 is a schematic diagram illustrating the formation of gas layers at the boundary of a person's blood stream and body tissue.

A gas layer forms wherever criterion (8) is violated, as shown in the schematic drawing of FIG. 2. Gas layers 18 form at the boundary between the blood stream 20 and body tissue 22. At such locations and times, equation (5) must give way to a requirement for mechanical equilibrium, $$p(x,t) = p_{N2}(x,t). \tag{9}$$

together with a formula for the rate of free gas formation:

$$GF(x,t) = -2\pi S_t D_t \int_{-\infty}^{t} \frac{\partial p(x,t')}{\partial t'} F\left[\frac{D_t(t-t')}{a^2}\right] dt'. \tag{9}$$

GF has units of pressure times volume per unit length and is a measure of the rate at which nitrogen mass is released as gas per unit length of capillary.

The rate of growth of nitrogen gas in the body is proportional to the number $N_c$ of active capillaries times the integral of GF along each capillary, less the rate at which free gas transpires through the lungs:

$$\frac{\partial G}{\partial t} = N_c \int_0^L GF(x,t) dx - \frac{G}{\theta}. \tag{10}$$

The first term on the right is the net source of nitrogen gas, and the second term is the rate at which the lungs exhale the gas. The transpiration time θ includes various delays as the gas layers break into bubbles and the bubbles make their way though the vascular system.

The final step in the mathematical model relates G to the total volume of nitrogen gas in the body:

$$V(t) = \frac{G(t)}{p_{N2}(L,t)}. \tag{11}$$

The gas volume is the total amount of nitrogen gas currently in the body divided by the partial pressure of nitrogen at the venous end of the capillary. The volume includes the contributions of the metabolic gases, but (11) is the correct formula for volume when G(t) represents the mass of nitrogen (partial pressure times volume) and $p_{N2}(L,t)$ is the partial pressure of nitrogen only.

Equations (1)-(11) represent the physics and physiology of the Gas Formation Model, but not the formulas used to provide output for displays. An example of such a formula is a sigmoid relationship between maximum gas volume and probability of decompression sickness. Such formulas will be obvious from the discussion of outputs and displays.

Memory Integral

The mathematical model includes four special aspects including the memory integral, inert gases other than nitrogen, multiple tissues, and forecasts of time remaining at depth and possible decompression procedures. All four give rise to specific patent claims.

The memory integral appears in equations (5) and (9). It expresses the amount of nitrogen gas stored in tissue as a function of the time derivative of nitrogen tension on the interior surface of the capillary. The integral extends over all past times t' and involves both past and current times in the integrand. To all appearances, the integral would have to be re-evaluated at each time step, a procedure costly of both computational time and memory. Fortunately there is an alternative, developed especially for the Gas Formation Model but of potential use for any system that involves time varying inputs to bounded storage media. The alternative replaces the memory integral with a set of differential equations having parameters related to the eigenvalues of a series similar to (6).

The memory integral of (5) and (9) can be written in the form $$\int_{-\infty}^{t} \frac{\partial p(x,t')}{\partial t'} F\left[\frac{D_t(t-t')}{a^2}\right] dt' = \pi r(x,t), \tag{12}$$

where

-continued $$r(x, t) = \sum_{n=1}^{\infty} c_n q_n(x, t), \quad (13)$$

$$q_n(x, t) = \int_{-\infty}^{t} \frac{\partial p(x, t')}{\partial t'} \exp[-\beta_n(t - t')] dt', \quad (14)$$

and $$\beta_n = D_t b_n^2 / a^2. \quad (15)$$

Equations (12)-(15) are nothing more than a restatement of the memory integral with the series representation (6) put in place of F. But now we notice that (14) is the solution of the partial differential equation $$\frac{\partial q_n(x, t)}{\partial t} = \frac{\partial p(x, t)}{\partial t} - \beta_n q_n(x, t). \quad (16)$$

Equation (16) can be solved in time step by step without explicit memory of events in the distant past. The need to remember events over an infinite sequence of past times t' has been replaced with an infinite series of terms $q_n$ evaluated at the current time t. In practice the series can be truncated to a few terms. The algorithm found in Appendix A uses eight terms.

Transformation of the memory integral into a set of differential equations affords an enormous reduction in computational time, typically by a factor of 1,000. The transformation, moreover, is of very general utility. It applies to the accumulation of a quantity in a bounded medium with internal transport subject to a linear partial differential equation. Examples can be found in the fields of heat transfer, chemical processors, nuclear power plants, and even auditorium acoustics. A curiosity of (16) is that it resembles the model for nitrogen accumulation in the "tissue compartments" of Haldane, but the temptation to identify the $q_n$'s with tissue compartments should be resisted. The $q_n$'s measure gas associated with the eigenmodes of a single homogeneous tissue medium. The time scales of the eigenmodes have as much to do with boundary conditions as tissue properties. Their values are not arbitrary but follow directly from the mathematical model.

Other Inert Gases

The GFM mathematical model is described for simplicity with nitrogen as the inert gas. With simple alterations, the same model can handle other inert gases and even mixtures of inert gases. Here is how GFM treats various gas mixtures.

Air

Air is a mixture of oxygen and nitrogen, the partial pressure of nitrogen being about 79% of the total. The GFM handles computations as described above with $R_{N2}=0.79$.

Nitrox

Nitrox is also a mixture of oxygen and nitrogen, but with a reduced percentage of nitrogen to forestall possible decompression sickness. GFM computes nitrox mixtures in the same way as air with a reduced value of $R_{N2}$.

Heliox

Heliox is a mixture of oxygen and helium. Helium reduces potential for nitrogen narcosis. GFM uses the appropriate value for $R_{He}$ and suitable values for the diffusivity of helium in tissue and solubilities of helium in tissue and blood. Otherwise computations proceed as with nitrogen.

Trimix

Trimix is a mixture of oxygen and both nitrogen and helium. Trimix has become popular among divers as an economical alternative to heliox. For trimix, the GFM computes blood tensions for nitrogen and helium separately and combines them only through the gas formation criterion $$p_{N2}(x,t) + p_{He}(x,t) \leq p_{amb}(t) + p_b(x,t) - p_o(x) \quad (16)$$

which replaces inequality (8). Of course the computation of free gas volume has to take both nitrogen and helium into account.

More exotic gas mixtures, for example with argon, are handled in the same way, with the sum on the left of (16) extending over all inert gases. In all cases, the metabolic gases (including water vapor) are treated as described in the section titled Mathematical Model.

Multiple Tissues

The GFM may be implemented to account for a single tissue model, or may be extended to compute nitrogen accumulation and elimination in multiple tissues. Each disparate tissue requires a distinct value of diffusivity and solubility, as well as a different values for b/a and $N_c$. Computations for multiple tissues proceed in parallel, with the free gas volumes evaluated separately, then combined into a single volume. These multiple tissues are not the "tissue compartments" of a Haldane model. Rather they represent truly distinct tissues of the human body: skeletal muscle, adipose tissue (fat), bone marrow, and perhaps brain matter. It should be noted that skeletal muscle is virtually the only tissue that responds to exercise. While vigorous exercise increases overall blood flow by a factor of three, almost all of the increase goes through the skeletal muscles where the blood flow increases by a factor of ten. Fat has five times the solubility of muscle, and bone marrow has a very low blood flow rate, which could account for the long time persistence of nitrogen in the body.

The parameters of the GFM algorithm listed in the Appendix represent average tissue properties. However, the GFM algorithm may be adapted to implement parallel computations relative to multiple tissues.

Predicting Futures

The GFM computes free gas volume and other quantities on the basis of past and current measurements of time, pressure, and exercise parameters. That is important but by no means sufficient. A divers' main interest is in the future. What does he need to do to get to the surface safely? To answer that question, a GFM dive computer needs to compute into the future under various ascent scenarios and inform the diver of his best options. Fortunately, the efficiency of the algorithm with differential equations in place of the memory integral allows the computation of alternative futures with ease.

Figure 3:
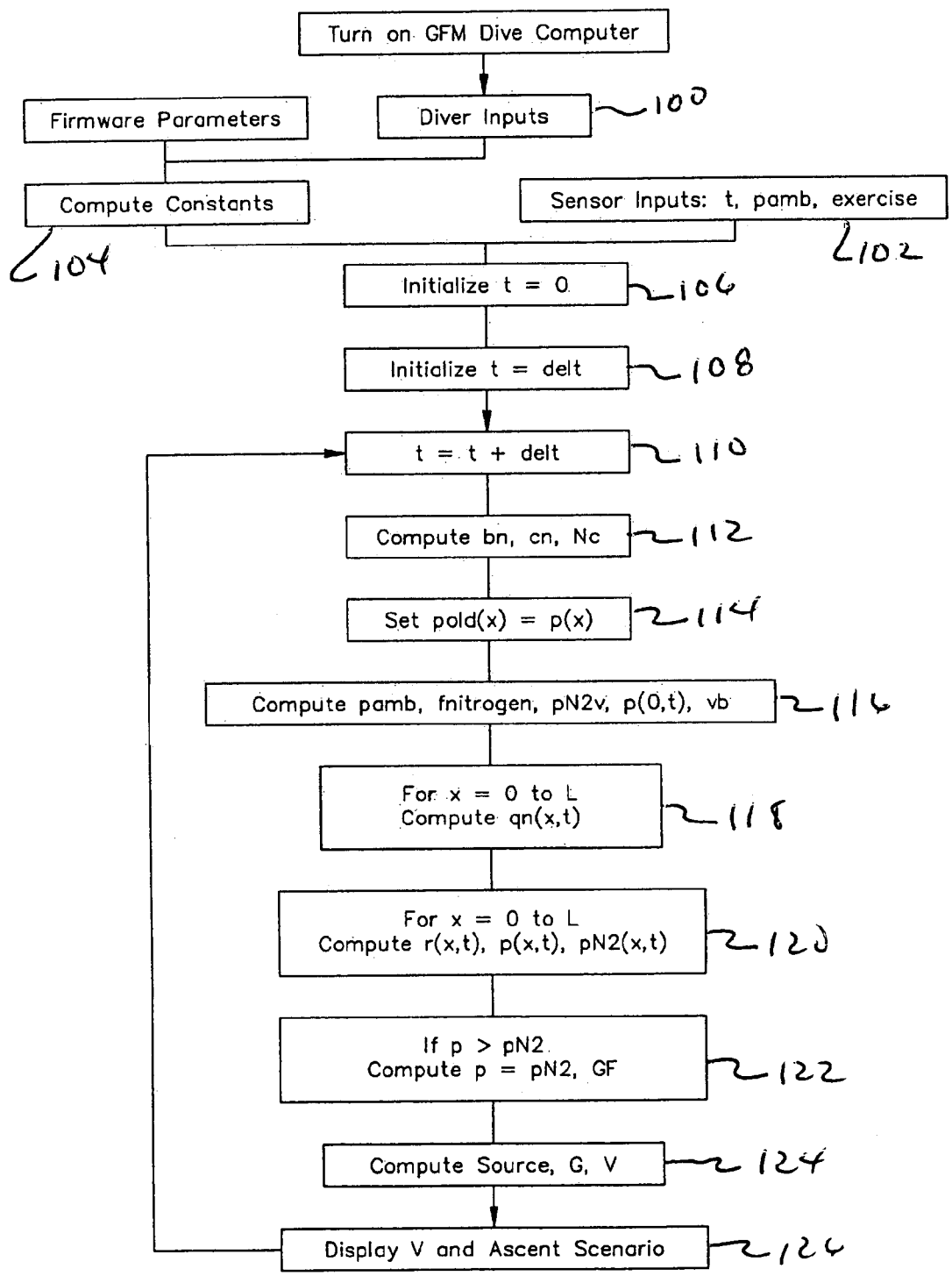
FIG. 3 is a flow chart illustrating a gas formation model, according to the invention.
Figure 4:
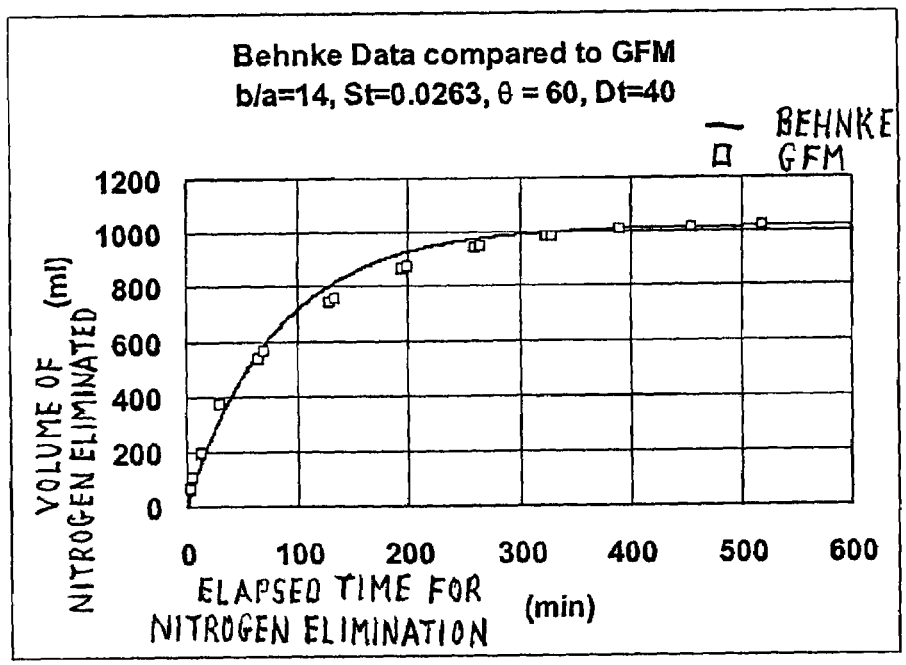
FIG. 4 is a plot of predictions by the gas formation model, according to the invention, compared with Behnke data.

GFM dive computers compute multiple dive scenarios through future times of, for example, one hour. FIGS. 3 and 4 show ascent scenarios under two circumstances.

GFM Algorithm

FIG. 3 is a simplified flow chart of a GFM algorithm. A complete listing of the algorithm coded in Virtual Basic run in the context of an Excel™ spreadsheet is included in Appendix A. Steps 100 and 102 require the inputting of parameters. These inputs include physiological parameters from firmware, inputs that the diver may enter into the dive computer, and inputs derived in real time from sensors. The real time sensor inputs include time, ambient pressure, water temperature, and may include a measure or measures of exercise level.

Constants are calculated in step 104 and time is initialized in steps 106 and 108. The main program loop includes steps 110, 112, 114, 116, 118, 120, 122, 124 and 126 and computes the number $N_c$ of active capillaries, eigenvalues $b_n$, and eigenmode amplitudes $c_n$ as functions of exercise level. It goes on to compute various functions of time, including the inert gas tension $p(0,t)$ at the arterial end of the capillary.

Within the main time loop are spatial loops to evaluate quantities as functions of location along the capillary. Those include the $q_n$'s as well as r, p, and $p_{N2}$, and the tensions of any other inert gases that may be present. The gas formation criterion tests the net inert gas tension and makes the appropriate downward adjustments if the criterion is exceeded. The local gas formation rates GF are computed and integrated over the capillary length to produce the total sources.

The main loop concludes by computing, in step 124, total free gas amounts G and volume V, the key variable for evaluating the diver's situation with regard to possible decompression phenomena.

Outputs

Some of the outputs of the GFM are unique to GFM. Like conventional counterparts, a GFM dive computer will include a dive planning function for use before a dive. Six of the outputs have to do with the primary variables of time and depth:
Current time
Current depth
Accumulated water time
Accumulated surface interval
Maximum past depth
Ascent rate
Four outputs concern air and oxygen management:
Tank pressure
Partial pressure of oxygen
Air time remaining
Oxygen time remaining
Three of the outputs are conventional outputs that are based on the novel GFM algorithm:
No-decompression (NoD) time remaining
Decompression obligations
Time to fly
Finally, five of the outputs are unique to the GFM algorithm:
Exercise level
Dissolved inert gas volume
Current free inert gas volume
Future free gas volume
Probability of decompression sickness ($P_{dcs}$)

The exercise level output is a simple index of exertion based on one or more of the measurement methods described above in the section titled Exercise. Exercise level is key to management of dive safety, since exercise has a strong influence on rates of accumulation and elimination of inert gas.

Dissolved inert gas volume is the GFM analogue of the "tissue loadings" of Haldane-based dive computers. The natural units are milliliters of gas at STP, though more intuitive units may be used for the actual display. Dissolved inert gas volume can be presented in graphical form to show to a diver the rise and fall of inert gas in his body. Current free gas volume will be zero during most of a dive but should be of great interest on the surface.

Future free gas volume is the most important output of a GFM dive computer. The output can be presented in graphical form for the time remaining at depth and the optimum ascent scenario. Plots of future free gas volume give divers profound insight into their situation with regard to safety from decompression sickness. Of special importance will be the maximum future free gas volume, which should remain below the critical gas volume explained in a subsequent section. Graphical output is especially interesting during safety or decompression stops, when the diver may monitor the elimination of future free gas from his body.

Probability of decompression sickness is related directly to the maximum future free gas volume through a sigmoid function developed from thousands of tests on decompression effects. Probability of decompression sickness may be a more intuitive output than maximum future free gas volume.

Parameter Selection

The GFM as currently implemented requires thirteen input parameters. Ten of them can be found in standard literature on physiology. Two must be derived from important experiments on nitrogen elimination by Behnke and Willmon (1941). The final parameter, transpiration time θ, involves special considerations and is deferred to the section called Transpiration.

Two of the parameters are blood pressures at the arterial and venous ends of the capillary, and those can be found in many sources. Scanlon and Sanders (1999) report that the arterial blood pressure just upstream of the capillaries is 30-35 mm Hg, and the venous blood pressure is 12-16 mm Hg. The selections below are appropriate and appear as inputs in the GFM listing of Appendix A:

$p_{ba}$=30 mm Hg Scanlon and Sanders (1999)

$p_{bv}$=12 mm Hg

Two more parameters are pressures, the sum of the partial pressures (tensions) of the metabolic or "other" gases including oxygen, carbon dioxide, and water vapor. Vann and Thalmann (1993) present the sum of the metabolic gases at the venous end of the capillaries as 131 mm Hg, and Hills (1977) argues that the sum should be nearly constant over most if not all of the capillary beds. Thus $p_{oa}$=131 mm Hg Hills (1977)

$p_{ov}$=131 mm Hg Vann and Thalmann (1993)

In his classic text on the circulation system, Burton (1968) presents values for the radius a and length L of capillaries, as well as for the average velocity $v_b$ of blood in the capillaries:

a=4 microns Burton (1968)

L=1000 microns $v_b$=24000 microns/min

Burton also provides a value of 300 ml for the volume $V_c$ of systemic capillaries. Equation (2) relates the number of capillaries to volume and other dimensions, from which we conclude that $N_c$=6.0×10$^9$ Burton (1968) and equation (2)

A further geometrical parameter is the effective radius b of tissue surrounding a capillary. Because the capillaries are highly elongated, the ratio b/a can be found from the ratio of total tissue volume to capillary volume:

$$b/a = \sqrt{V_t/V_c}.$$

Xu, Chao, and Bozkurt (2000) indicate that a person who weighs 70 kg has a typical tissue volume of 60,000 ml, from which b/a=14 Xu et al. (2000)

Weathersby and Homer (1980) provide a value for the solubility of nitrogen in whole blood:

$S_b$=0.0148 ml/ml Weathersby and Homer (1980)

To obtain the other two parameters, we must turn from standard physiology literature to the experiments of Behnke and Willmon (1941), who provide data on nitrogen elimination from a subject saturated with air at one atmosphere. They found the total amount of nitrogen to be 1076 ml evaluated at STPD, meaning standard temperature and temperature dry (1 atm, 0° C.).

The measured nitrogen volume must be altered in several ways to produce a solubility for the GFM algorithm. The solubility used in the algorithm is the volume of nitrogen in tissue at body temperature, saturated under a nitrogen partial pressure of one atmosphere or 760 mm Hg. The Behnke and Willmon experiments involved a nitrogen partial pressure of 0.79(760−46)=564 mm Hg, where the correction of 46 mm Hg allows for water vapor in the lungs. Correcting to a partial pressure of 760 mm Hg increases the measured volume by a factor of 1.35, and correcting to body temperature increases the volume by a further factor of 310/273=1.14. Tissue at body temperature under one atmosphere of nitrogen would absorb 1029×1.35×1.14=1577 ml of nitrogen. Using Xu et al.'s value for tissue volume, we find the solubility of nitrogen in tissue:

$S_t$=0.0263 ml/ml Behnke and Willmon (1941), Xu et al. (2000)

To evaluate the tissue diffusion coefficient, we turn to the GFM model of diffusion in the body. The plot of FIG. 4 below shows the results of fitting the time history of nitrogen elimination as computed by the GFM algorithm to the data of Behnke and Willmon. The value $D_t$=40 microns$^2$/min Behnke and Willmon (1941) and GFM provides the best fit and is our selection for the tissue diffusion coefficient.

Figure 5:
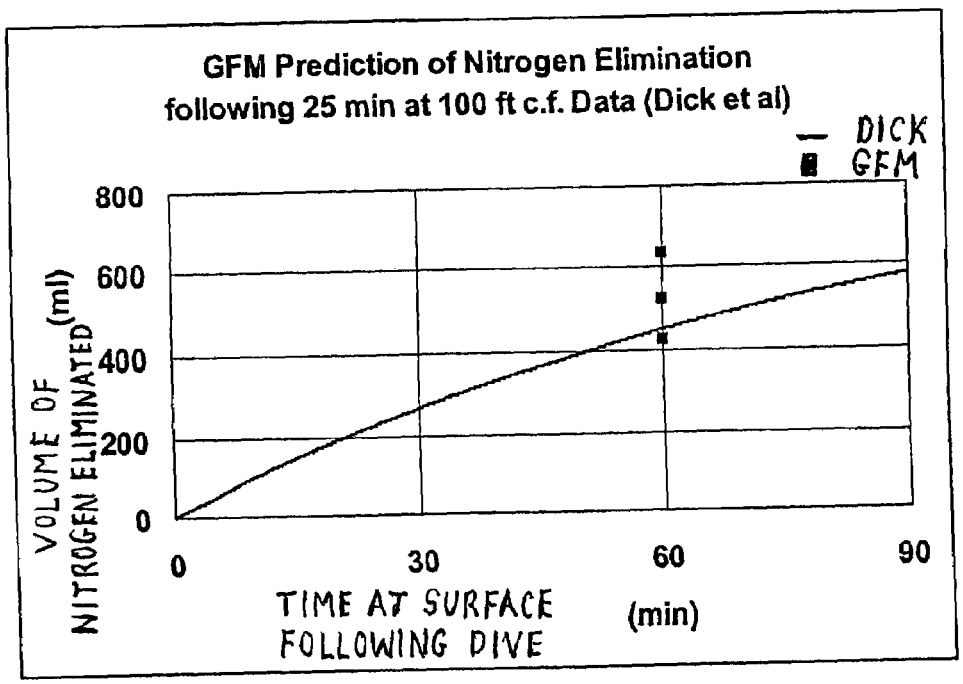
FIG. 5 is a graph of predictions by the gas formation model, according to the invention, of nitrogen elimination compared to measured data.

It is equally important to compare GFM predictions with examples that include absorption during compression, and Dick et al (1984) provides such data. An example of the comparison of GFM nitrogen elimination predictions with measured data following 25 minutes at 100 feet, as shown in the plot of FIG. 5, where the prediction is within the scatter of the data.

Critical Volume

When a diver is exposed to increased ambient pressure, nitrogen is absorbed in tissue. During the decompression following a dive, this gas diffuses from tissue into the blood and is transpired out of the body by the lungs during respiration. Most of this gas remains in solution, but under common conditions some is in the form of free gas. It is the later that is responsible for decompression sickness, with the body able to tolerate a critical volume.

Figure 6:
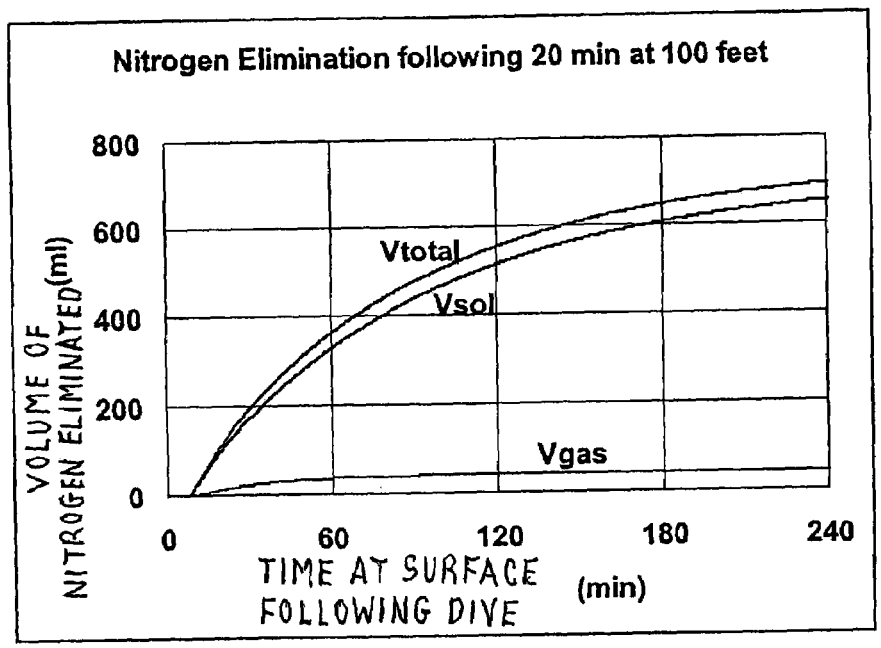
FIG. 6 is a plot of gas formation model calculations of gas released from a solution, according to the invention.

An example of GFM calculations of the gas release that comes from solution and that in the form of free gas is shown in the plot of FIG. 6. As can be seen, the majority of the gas release is from nitrogen that is dissolved in the blood, but a small portion has formed free gas.

Figure 7:
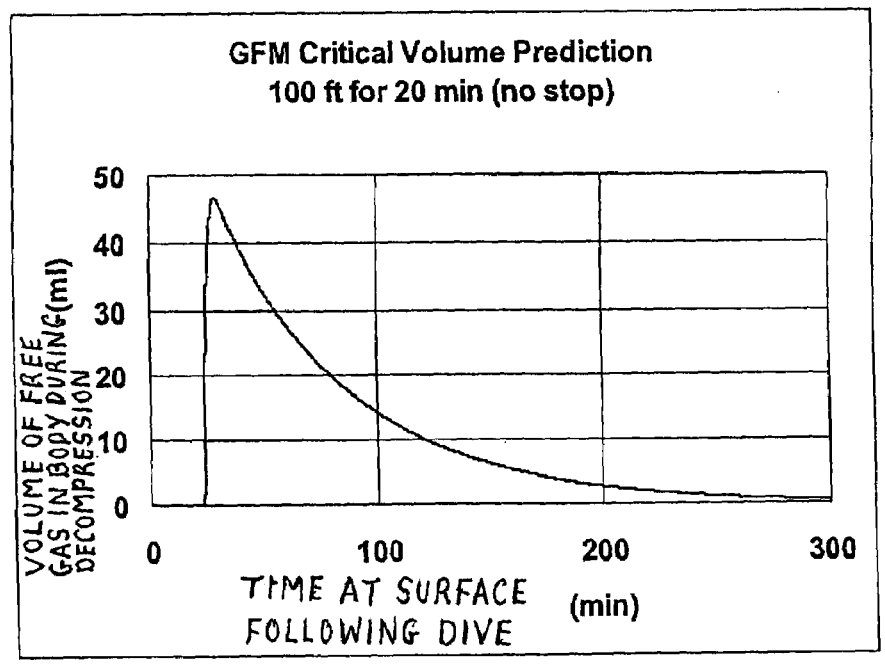
FIG. 7 is a graph of gas formation model calculations of free gas remaining in the body, according to the invention.

An example of the free gas remaining in the body during decompression is shown in FIG. 7. Initially the volume of free gas rises rapidly, but as gas is transpired by the lungs it reaches a maximum, and the maximum volume that the body can tolerate is the critical volume.

Figure 9:
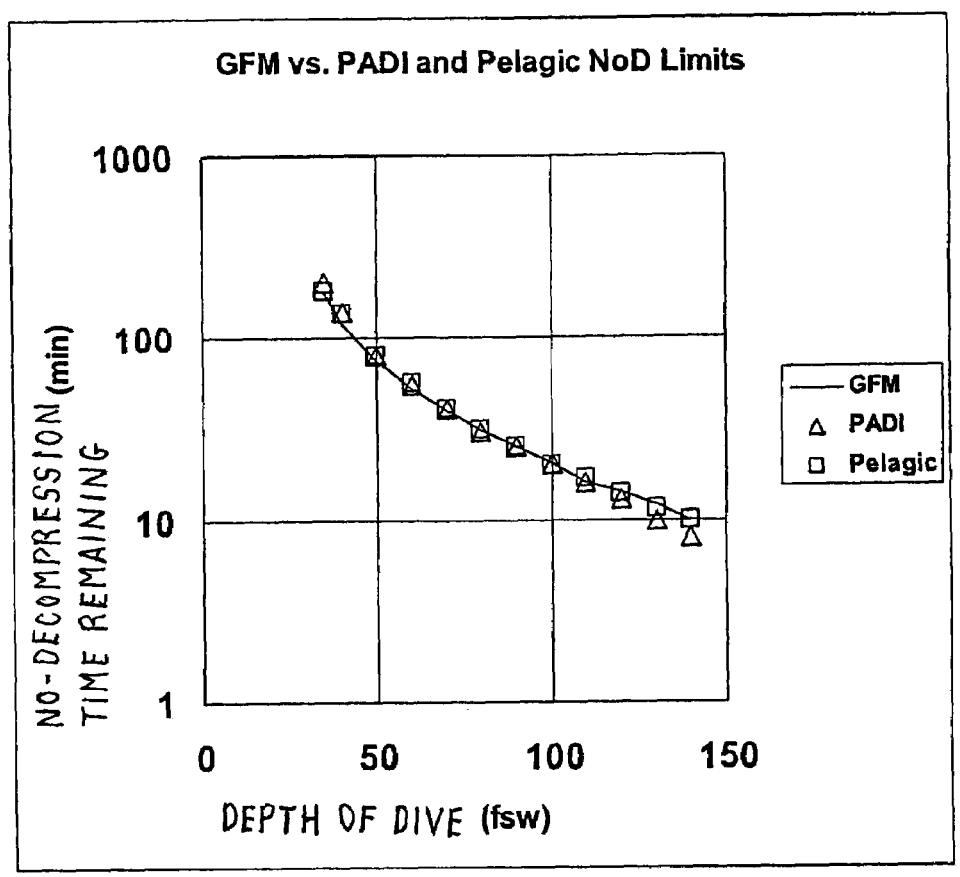
FIG. 9 is a plot of the data of FIG. 8.

GFM calculates a maximum free gas volume of 47 ml for a 20 minute exposure at 100 feet. Using this value as a critical volume, GFM predicts NoD limits that are presented in the table of FIG. 8 and the plot of FIG. 9 compared to PADI and data supplied by Lewis (2005) for Pelagic dive computers.

Transpiration

Figure 10:
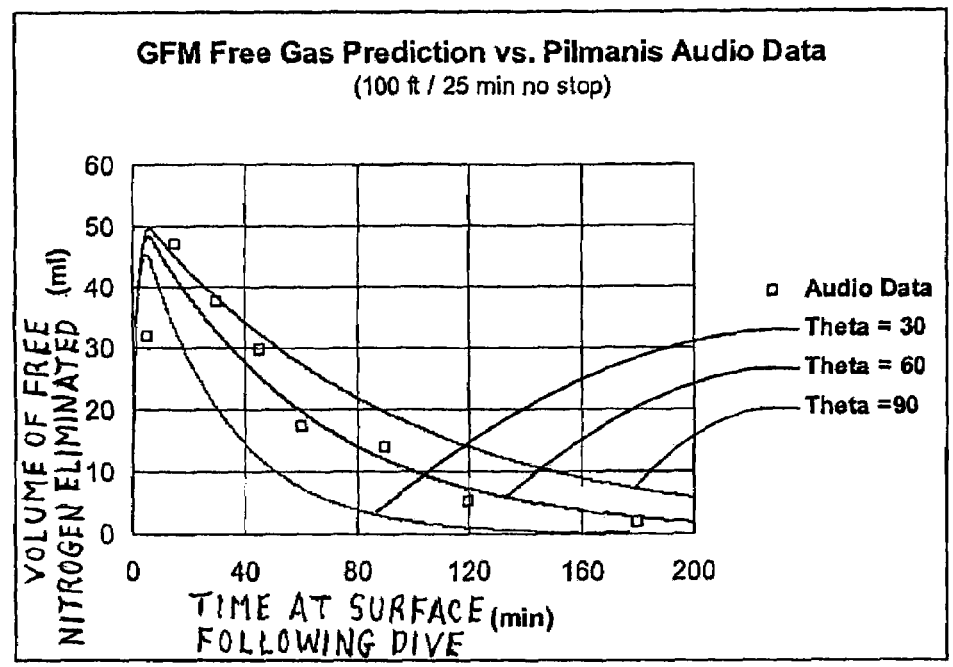
FIG. 10 is a graph of a qualitative comparison between audio data and gas formation model predictions.
Figure 11:
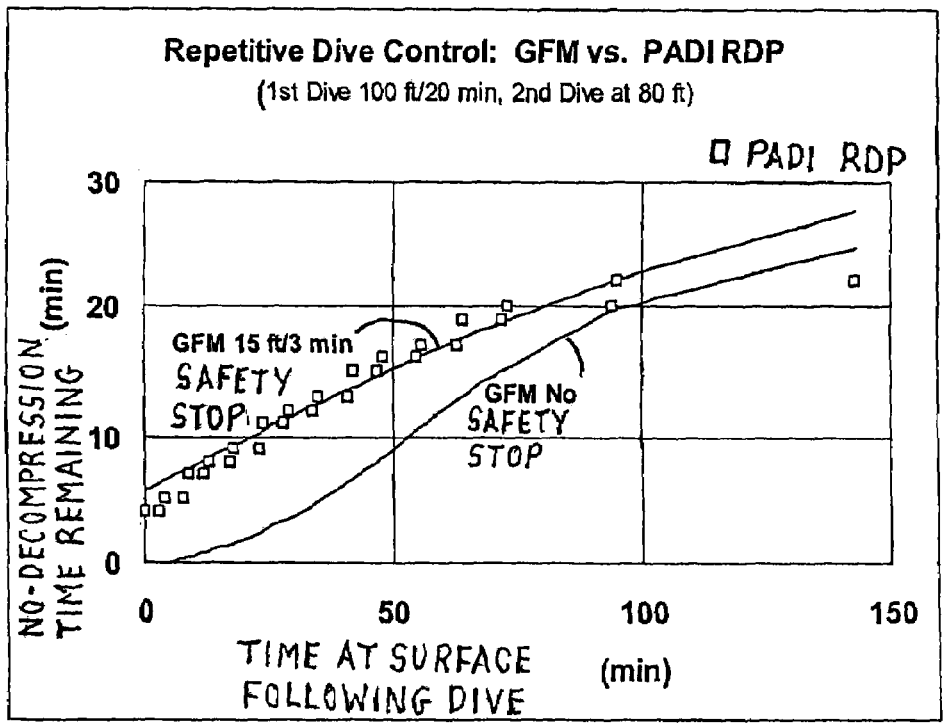
FIG. 11 is a plot comparing gas formation model calculations with PADI RDP data for repetitive dives.

There is one final computational parameter that must be selected, and that is the transpiration time constant, θ, that governs the elimination of free nitrogen gas by the lungs. Pilmanis (1976) Doppler monitored divers following exposures at several depths, and the time scale of these data provides a basis for selecting θ. The graph of FIG. 10 illustrates the qualitative comparison between these audio data and GFM free gas predictions for several values of θ, and it is clear that a value of θ=60 minutes provides the best fit.

Repetitive diving is limited both by residual nitrogen content of tissue and residual free gas, and θ plays an important role, particularly for short surface intervals. Just as was the case for single dive NoD limits, it is important to validate GFM predictions for repetitive dives. Since the PADI RDP is more conservative than the test data (Hamilton et al 1994), it represents a convenient basis for comparison with GFM. Many examples have been calculated, and typical results are illustrated in the plots below. Here an initial dive to 100 feet for the NoD limit of 20 minutes is followed by a repetitive dive to depths of 60 and 80 feet with a varying surface interval.

As can be seen, without a safety stop GFM is very conservative for the first 60 minutes. Following the PADI required 3 min safety stop at 15 feet, however, GFM predicts NoD limits for the repetitive dives that are in close agreement with the RDP. In summary, a value of θ=60 min is selected as being in agreement with the time dependence of the Doppler data of Pilmanis, and the agreement with the PADI RDP for repetitive diving demonstrates the overall validation of GFM for repetitive diving.

Display

Figure 12:
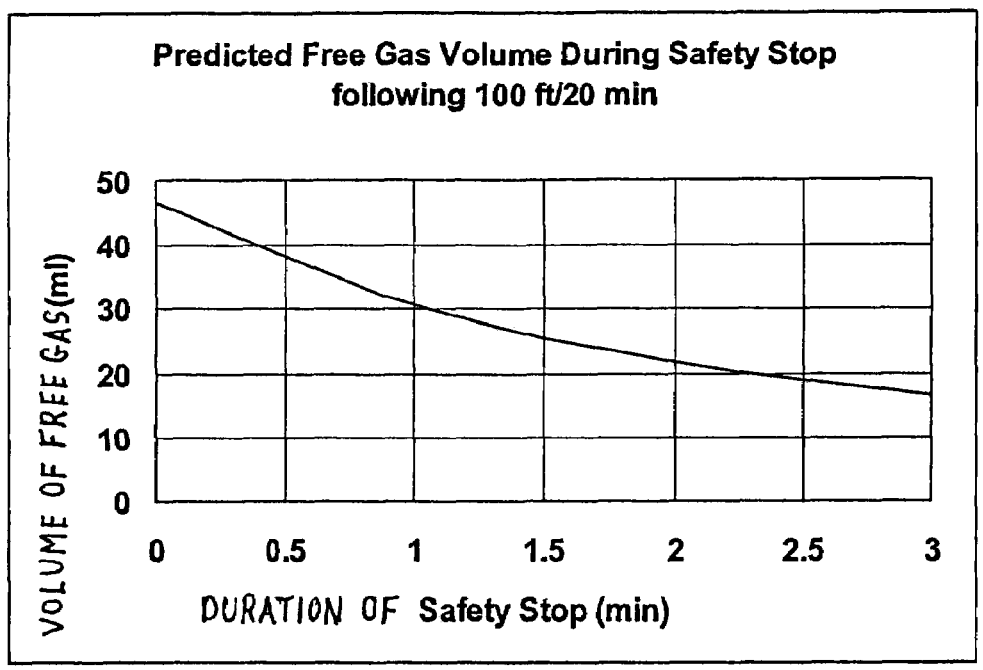
FIG. 12 is a graph predicting free gas volume during safety stops, using the gas formation model.

GFM calculations provide the typical data that are important for divers, e.g., NoD time remaining, decompression obligations, nitrogen tissue loading, etc. However, GFM has a unique capability that represents an important display option. This is the prediction of the maximum free gas volume that will occur following surfacing. While nitrogen tissue loading is interesting, it is the critical free gas volume that controls NoD limits and repetitive dives. Further, while the nitrogen tissue loading changes little during a safety stop, the free gas volume changes rapidly and dramatically providing the diver with considerable incentive to use the safety stop, as illustrated by the graph of FIG. 12.

Figure 13:
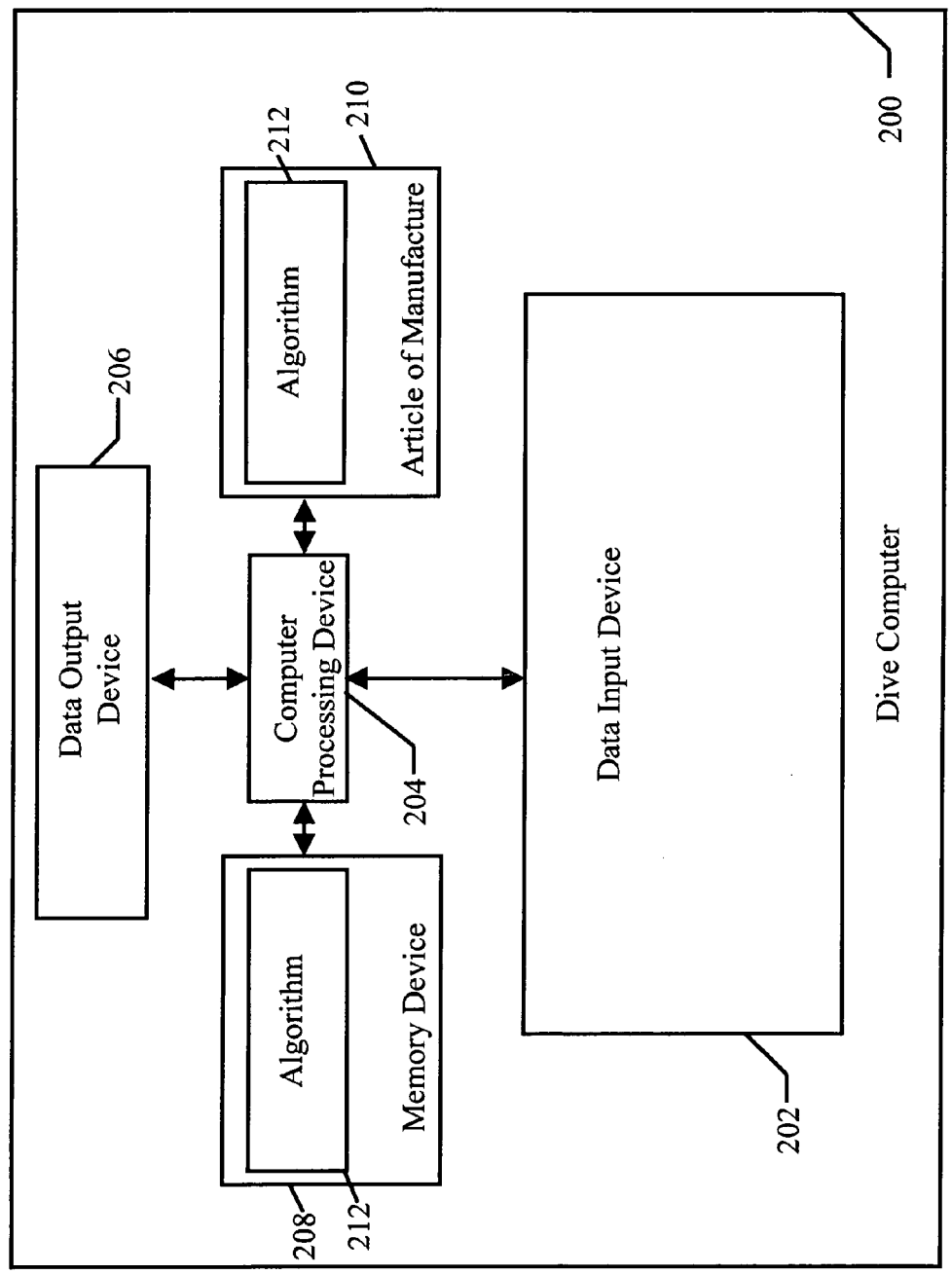
FIG. 13 is a block diagram illustrating a dive computer including a data input device, a computer processing device, and a data output device.

FIG. 13 is a block diagram of a dive computer 200 including a data input device 202, a computer processing device 204, and a data output device 206. A memory device 208 or an article of manufacture 210 may contain an algorithm 212 for calculating a value corresponding to formation of free inert gas in the body of a diver.

The data input device 202 may include a sensor, such as a pulse rate detector or oxygen use detector, or may include a plurality of buttons through which a user of the dive computer may manually enter data. The computer processing device 204 may include an FPGA, an ASIC, a programmable logic device ("PLD"), a complex PLD, a general purpose processor, a micro-processor, a micro-controller, or other computational device. The data output device may include a graphic display, one or more audio tones, or an interface to communicate with other external devices (not shown) such as a printer.

APPENDIX A

CODED GFM ALGORITHM

```
Dim hs As Double, pg As Double, ps As Double
Dim ve As Double, vr As Double, tr As Double
Dim rd As Double, db As Double, ra1 As Double, ds1 As Double
Dim ra2 As Double, ds2 As Double, ra3 As Double, rc As Double,
hc As Double
Dim t1 As Double, t2 As Double, t3 As Double, t4 As Double,
t5 As Double
Dim t6 As Double, t7 As Double, t8 As Double, t9 As Double,
t10 As Double
Dim RN2 As Double
Sub Decomp12( )
Dim ns As Integer
Dim nt As Integer
Dim nx As Integer
Dim b(1 To 8) As Double
Dim c(1 To 8) As Double
Dim beta(1 To 8) As Double
Dim p(0 To 20) As Double
Dim pold(0 To 20) As Double
Dim poldold(0 To 20) As Double
Dim q(1 To 8, 0 To 20) As Double
Dim GF(0 To 20) As Double
'Physiological Parameters
a = 4
L = 1000
St = 0.0274
Sb = 0.0137
Dt = 38
Nc = 6090000000#
theta = 25
vdot = 0.4
'Blood Pressure Parameters
poa = 131
pov = 131
pba = 30
pbv = 12
'Water Level
hs = 0
'Dive Profile
td = 2
rd = 60
db = 120
tb = 12
ra1 = 60
ds1 = 0
ts1 = 40
ra2 = −60
ds2 = 55
ts2 = 48
ra3 = 60
'Flight Profile
tf = 180
rc = 1000
hc = 0
'Blood Velocity Profile
ve = 24000
vr = 24000
tr = 120
'Nitrox Ratio
RN2 = 0.79
'Computational Parameters
delt = 0.1
tmax = 200
delx = 0.05
'F Parameters
b(1) = 0.07203
b(2) = 0.34177
b(3) = 0.58973
b(4) = 0.83462
b(5) = 1.07831
```

APPENDIX A-continued

CODED GFM ALGORITHM

```
b(6) = 1.32137
b(7) = 1.56406
b(8) = 1.80652
c(1) = 0.15577
c(2) = 0.0651
c(3) = 0.05719
c(4) = 0.05412
c(5) = 0.05253
c(6) = 0.05159
c(7) = 0.05097
c(8) = 0.05055
'Computed Constants
Pi = 4 * Atn(1)
J = 2 * St * Dt * L / (Sb * a ^ 2)
K = 2 * Pi * St * Dt * L
alpha = Dt / a ^ 2
delpa = poa − pba
delpv = pov − pbv
For ns = 1 To 8
    beta(ns) = alpha * b(ns) ^ 2
Next
pg = 760 / 33
ps = 760 * (1 − 0.0000068634 * hs) ^ 5.2583
'Computed Times
t1 = td
If rd < 1 Then
    t2 = t1
Else
    t2 = t1 + Abs(db / rd)
End If
t3 = t2 + tb
t4 = t3 + Abs((db − ds1) / ra1)
t5 = t4 + ts1
t6 = t5 + Abs((ds1 − ds2) / ra2)
t7 = t6 + ts2
t8 = t7 + Abs(ds2 / ra3)
t9 = t8 + tf
t10 = t9 + Abs((hc − hs) / rc)
'Time 0
t = 0
nt = 10
pambient = pamb(t)
fnitrogen = FN2(t)
pN2v = pambient − delpv
p(0) = fnitrogen * (pambient − 47)
For nx = 0 To 20
    p(nx) = p(0)
    For ns = 1 To 8
        q(ns, nx) = 0
    Next ns
Next nx
Source = 0
G = 0
V = 0
Worksheets("Sheet1").Cells(nt, 1) = t
Worksheets("Sheet1").Cells(nt, 2) = pambient
Worksheets("Sheet1").Cells(nt, 3) = p(20)
Worksheets("Sheet1").Cells(nt, 4) = Source
Worksheets("Sheet1").Cells(nt, 5) = V
'Time delt
For nx = 0 To 20
    pold(nx) = p(nx)
Next nx
t = t + delt
nt = nt + 1
pambient = pamb(t)
fnitrogen = FN2(t)
pN2v = pambient − delpv
p(0) = fnitrogen * (pambient − 47)
For nx = 0 To 20
    p(nx) = p(0)
    For ns = 1 To 8
        q(ns, nx) = 0
    Next ns
Next nx
Source = 0
G = 0
```

APPENDIX A-continued

CODED GFM ALGORITHM

```
    V = 0
    Worksheets("Sheet1").Cells(nt, 1) = t
    Worksheets("Sheet1").Cells(nt, 2) = pambient
    Worksheets("Sheet1").Cells(nt, 3) = p(20)
    Worksheets("Sheet1").Cells(nt, 4) = Source
    Worksheets("Sheet1").Cells(nt, 5) = V
'Time Loop
Do While t <= tmax - delt / 2
    For nx = 0 To 20
        poldold(nx) = pold(nx)
        pold(nx) = p(nx)
    Next nx
    t = t + delt
    nt = nt + 1
    pambient = pamb(t)
    fnitrogen = FN2(t)
    pN2v = pambient - delpv
    p(0) = fnitrogen * (pambient - 47)
    velocity = vel(t)
    For nx = 0 To 20
        GF(nx) = 0
        For ns = 1 To 8
            q(ns, nx) = q(ns, nx) + pold(nx) - poldold(nx) - beta(ns) *
            delt * q(ns, nx)
        Next ns
    Next nx
    For nx = 1 To 20
        r = 0
        For ns = 1 To 8
            r = r + c(ns) * q(ns, nx)
        Next ns
        p(nx) = p(nx - 1) - J * Pi * delx * r / velocity
        If p(nx) < 0 Then p(nx) = 0
        x = nx * delx
        pN2 = pN2v + (delpa - delpv) * (x - 1)
        If p(nx) > pN2 Then
            p(nx) = pN2
            GF(nx) = -K * Pi * r
        End If
    Next nx
    Source = 0
    For nx = 0 To 20
        Source = Source + GF(nx) * delx
    Next nx
    Source = Source * Nc / 1000000000000#
    G = G + delt * (Source - G / theta)
    'G = G + delt * (Source - pN2v * vdot)
    If G < 0 Then G = 0
    V = G / pN2v
    Worksheets("Sheet1").Cells(nt, 1) = t
    Worksheets("Sheet1").Cells(nt, 2) = pambient
    Worksheets("Sheet1").Cells(nt, 3) = p(20)
    Worksheets("Sheet1").Cells(nt, 4) = Source
    Worksheets("Sheet1").Cells(nt, 5) = V
Loop
End Sub
Function pamb(t)
If rd < 1 Then
    If t < t3 Then
        pamb = ps + pg * db
    ElseIf t < t4 Then
        pamb = ps + pg * db - pg * (t - t3) * ra1
    ElseIf t < t5 Then
        pamb = ps + pg * ds1
    ElseIf t < t6 Then
        pamb = ps + pg * ds1 - pg * (t - t5) * ra2
    ElseIf t < t7 Then
        pamb = ps + pg * ds2
    ElseIf t < t8 Then
        pamb = ps + pg * ds2 - pg * (t - t7) * ra3
    ElseIf t < t9 Then
        pamb = ps
    ElseIf t < t10 Then
        z = hs + (t - t9) * rc
        pamb = 760 * (1 - 0.0000068634 * z) ^ 5.2583
    Else
        z = hc
```

APPENDIX A-continued

CODED GFM ALGORITHM

```
        pamb = 760 * (1 - 0.0000068634 * z) ^ 5.2583
    End If
Else
    If t < t1 Then
        pamb = ps
    ElseIf t < t2 Then
        pamb = ps + pg * (t - t1) * rd
    ElseIf t < t3 Then
        pamb = ps + pg * db
    ElseIf t < t4 Then
        pamb = ps + pg * db - pg * (t - t3) * ra1
    ElseIf t < t5 Then
        pamb = ps + pg * ds1
    ElseIf t < t6 Then
        pamb = ps + pg * ds1 - pg * (t - t5) * ra2
    ElseIf t < t7 Then
        pamb = ps + pg * ds2
    ElseIf t < t8 Then
        pamb = ps + pg * ds2 - pg * (t - t7) * ra3
    ElseIf t < t9 Then
        pamb = ps
    ElseIf t < t10 Then
        z = hs + (t - t9) * rc
        pamb = 760 * (1 - 0.0000068634 * z) ^ 5.2583
    Else
        z = hc
        pamb = 760 * (1 - 0.0000068634 * z) ^ 5.2583
    End If
End If
End Function
Function vel(t)
If t < t8 Then
    vel = ve
ElseIf t < t8 + tr Then
    vel = ve - (ve - vr) * (t - t8) / tr
Else
    vel = vr
End If
End Function
Function FN2(t)
If t < t1 Then
    FN2 = 0.79
ElseIf t < t1 + 1 Then
    FN2 = 0.79 + (t - t1) * (RN2 - 0.79) / 1
ElseIf t < t8 - 1 Then
    FN2 = RN2
ElseIf t < t8 Then
    FN2 = RN2 + (t - t8 + 1) * (0.79 - RN2) / 1
Else: FN2 = 0.79
End If
End Function
```

Those skilled in the art of modeling the formation of free nitrogen in the human body may develop other embodiments of the present invention. However, the terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A dive computer, comprising:
   a processor connected to a memory;
   a pressure transducer connected to the processor;
   a clock circuit connected to the processor;
   wherein the processor and the pressure transducer are configured to measure depth;
   wherein the processor and clock circuit are configured to measure the passage of time;

wherein the processor is configured to calculate the amount of inert gas absorbed by the body tissue of a diver during a dive using at least the measurements of depth and the passage of time; and wherein the processor is configured to calculate a prediction of the volume of free gas that will form in the blood vessels of a diver during and after ascent using at least the depth measurement and the calculation of the amount of inert gas absorbed by the body tissue of the diver.

2. The dive computer of claim 1, wherein calculating the predicted volume of free gas that will form in the blood vessels of a diver includes calculating a free gas layer that will form on a surface within the body of the diver.

3. The dive computer of claim 1, wherein the predicted volume of free gas that will form in the blood vessels of a diver is a maximum volume of said free gas.

4. The dive computer of claim 1, wherein the predicted volume of free gas that will form in the blood vessels of a diver is a calculation of the maximum volume of free gas resulting from an ascent procedure.

5. The dive computer of claim 4, wherein the processor is adapted to calculate a dive profile, including an ascent procedure, that limits the predicted maximum volume of free gas that will form in the blood vessels of a diver as a result of decompression during the ascent procedure to a predetermined value.

6. The dive computer of claim 5, wherein said ascent procedure includes an ascent rate.

7. The dive computer of claim 5, wherein said dive profile includes a time and a corresponding depth that will not require a decompression stop during said ascent procedure.

8. The dive computer of claim 5, wherein said ascent procedure includes a decompression stop.

9. The dive computer of claim 1, further comprising a data input device for receiving an input and transmitting the input to the processor, and wherein the processor is adapted to receive the input from the data input device.

10. The dive computer of claim 9, wherein the data input device is adapted to manually receive information from the diver.

11. The dive computer of claim 9, wherein the data input device includes a sensor.

12. The dive computer of claim 11, wherein:
the sensor is configured to generate a signal indicative of the exercise level of the diver;
the processor is configured to calculate the amount of inert gas absorbed by the body tissue of a diver during a dive using information indicative of the exercise level of the diver.

13. The dive computer of claim 11, wherein:
the sensor is configured to generate a signal indicative of the pulse rate of the diver;
the processor is configured to calculate the amount of inert gas absorbed by the body tissue of a diver during a dive using information indicative of the pulse rate of the diver.

14. The dive computer of claim 11, wherein:
the sensor is configured to generate a signal indicative of the oxygen consumption of the diver;
the processor is configured to calculate the amount of inert gas absorbed by the body tissue of a diver during a dive using information indicative of the oxygen consumption of the diver.

15. The dive computer system of claim 1, wherein:
the processor is configured for calculating a quantity of free gas within the body of a diver;

the processor is adapted to utilize a memory integral for evaluating inert gas storage in the body of the diver, said memory integral having time as both the upper limit of the integration and as a variable in the integrand.

16. The gas formation system of claim 15, wherein the processor is adapted to transform the memory integral into a set of differential equations.

17. The dive computer of claim 1, wherein the processor is adapted to calculate a probability of the diver experiencing decompression sickness using the predicted volume of free gas that will form in the blood vessels of a diver during and after ascent.

18. The dive computer of claim 1, further comprising a data output device for displaying an output.

19. The dive computer of claim 18, wherein:
the processor is configured to calculate the volume of free gas present in the blood vessels of a diver using at least the depth measurements and the calculations of inert gas absorbed by the body of a diver
the output displayed on the data output device includes the volume of free gas within the blood vessels of the diver.

20. The dive computer of claim 19, wherein the output includes a graphical representation of the estimate of the volume of free gas within the blood vessels of the diver.

21. The dive computer of claim 18, wherein the output displayed on the data output device includes a predicted maximum volume of free gas that will form within the blood vessels of the diver during and after ascent.

22. The dive computer of claim 18, wherein the output includes a recommended ascent rate.

23. The dive computer of claim 18, wherein the output includes a time remaining at a depth that does not require a decompression stop during an ascent.

24. The dive computer of claim 18, wherein the output includes information concerning a decompression stop during an ascent.

25. A method of determining safe ascent procedures for a diver during a dive, comprising:
determining depth and time during a dive;
determining the amount of inert gas absorbed by the body tissue of the diver during the dive;
calculating a prediction of the volume of free gas that will form in the blood vessels of the diver during and after ascent based upon the depth of the diver and the amount of inert gas absorbed by the body tissue of the diver; and
providing the diver with recommendations concerning ascent procedures based upon the prediction of the volume of free gas that will form in the blood vessels of the diver during and after ascent.

26. The method of claim 25, wherein determining the amount of inert gas absorbed by a diver further comprises measuring the exercise level of the diver.

27. The method of claim 25, wherein determining the amount of inert gas absorbed by a diver further comprises measuring the pulse rate of the diver.

28. The method of claim 25, wherein determining the amount of inert gas absorbed by a diver further comprises measuring the oxygen consumption of the diver.

29. The method of claim 25, wherein calculating a prediction of the volume of free gas that will form in the blood vessels of the diver during and after ascent further comprises estimating the free gas that will form on the surface of the blood vessels of the diver.

30. The method of claim 29, wherein estimating the free gas that will form on the surface of the blood vessels of the diver further comprises estimating the free gas that will form in annular rings on the surface of the blood vessels of the diver.

31. The method of claim 25, further comprising calculating a prediction of the volume of free gas that will form in the blood vessels of the diver using at least the determined amount of inert gas absorbed in the body tissue of the diver, a previous prediction of the volume of free gas in the blood vessels of the diver and the determined depth.

32. The method of claim 31, further comprising displaying the prediction of the current volume of free gas in the blood vessels of the diver.

33. The method of claim 25, further comprising displaying a prediction of the maximum volume of free gas that will form in the blood vessels of the diver during and after ascent in accordance with the recommended ascent procedures.

* * * * *